United States Patent [19]

Lang et al.

[11] Patent Number: 4,871,734
[45] Date of Patent: Oct. 3, 1989

[54] SUBSTITUTED THIENOIMIDAZOLE-TOLUIDINE DERIVATIVES AS INHIBITORS OF GASTRIC ACID SECRETION

[75] Inventors: Hans-Jochen Lang, Hofheim am Taunus; Manfred Rösner, Eppstein/Taunus; Weidmann, Klaus, Kronberg/Taunus; Robert Rippel, Hofheim am Taunus; Andreas W. Herling, Dreieich, all of Fed. Rep. of Germany

[73] Assignee: Hoechst Aktiengesellschaft, Frankfurt am Main, Fed. Rep. of Germany

[21] Appl. No.: 123,262

[22] Filed: Nov. 20, 1987

[30] Foreign Application Priority Data

Nov. 22, 1986 [DE] Fed. Rep. of Germany ....... 3639926

[51] Int. Cl.$^4$ ............... A61K 31/55; C07D 495/04
[52] U.S. Cl. ................... 514/212; 514/228.5;
514/232.8; 514/234.2; 514/253; 514/316;
514/322; 514/338; 514/393; 540/544; 540/597;
540/598; 540/603; 544/58.7; 544/60; 544/61;
544/80; 544/121; 544/129; 544/139; 544/370;
546/187; 546/199; 546/271; 548/215; 548/240;
548/323
[58] Field of Search ............ 548/323, 215, 240;
544/58.7, 60, 80, 61, 120, 139, 129, 370;
546/199, 187, 271; 514/322, 312, 228.5, 316,
338, 232.8, 253, 393; 540/594, 597, 598, 603

[56] References Cited

U.S. PATENT DOCUMENTS 3,506,678 4/1970 Hoff et al. ............... 548/323 X
4,045,563 8/1977 Berntsson et al. ............. 548/327 X
4,472,409 9/1984 Senn-Bilfinger ............. 546/271 X
4,585,775 4/1986 Hitzel et al. ............. 514/287

FOREIGN PATENT DOCUMENTS 0005129 10/1979 European Pat. Off. ........... 546/271
3509333 9/1986 Fed. Rep. of Germany ...... 546/271

*Primary Examiner*—Richard A. Schwartz
*Attorney, Agent, or Firm*—Finnegan, Henderson, Farabow, Garrett, & Dunner

[57] ABSTRACT

Thienoimidazole-toluidines of the formula I

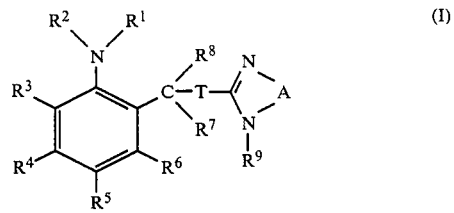

in which
A represents

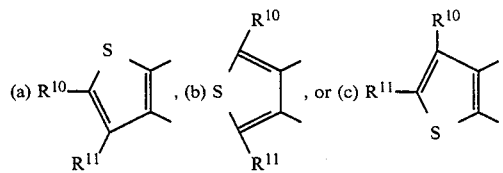

T denotes —S—, —SO— or —SO$_2$—, and R$^1$ to R$^9$ have the meanings stated in the description, and a process for their preparation, pharmaceutical compositions containing them, and their use as inhibitors of gastric acid secretion, are described.

12 Claims, No Drawings

SUBSTITUTED THIENOIMIDAZOLE-TOLUIDINE DERIVATIVES AS INHIBITORS OF GASTRIC ACID SECRETION

Benzimidazole derivatives having an inhibitory action on gastric acid secretion are disclosed in, for example, DE-A 2,548,340, EP-A 5129, DE-A 3,240,248, DE-A 3,333,314 and DE-A 3,509,333.

It has now been found, surprisingly, that certain substituted thienoimidazole-toluidines are highly active inhibitors of gastric acid secretion.

The present invention relates to thienoimidazole-toluidines of the formula I

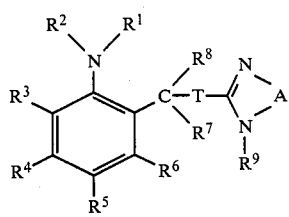

in which
A represents

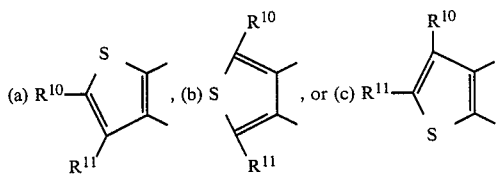

T denotes —S—, —SO— or —SO$_2$—, $R^1$ and $R^2$ are identical or different and denote hydrogen, ($C_1$-$C_6$)-alkyl, ($C_3$-$C_6$)-cycloalkyl, ($C_3$-$C_6$)-alkenyl or ($C_3$-$C_6$)-alkynyl, or $R^1$ and $R^2$ together represent a methylene chain —[CH$_2$]$_n$—, which can contain a double bond, in which n is 2, 3, 4, 5 or 6, and in which a methylene group can be replaced by oxygen, sulfur or NR$^{12}$, $R^3$, $R^4$, $R^5$ and $R^6$ are identical or differenet and represent hydrogen, halogen, cyano, trifuloromethyl, benzyloxy, ($C_1$-$C_6$)-alkyl-Y or phenyl-Y, in which Y denotes oxygen, sulfur, sulfinyl, sulfonyl or —[CH$_2$]$_m$— with m denoting 0, 1 or 2, —CO—R$^{13}$, —SO$_2$NR$^{14}$R$^{15}$, —O—COR$^{14}$, —NR$^{14}$—COR$^{15}$, —NR$^{14}$—SO$_2$R$^{15}$ or —NR$^{14}$R$^{15}$, $R^7$ and $R^8$ are identical or different and denote hydrogen or methyl, $R^9$ denotes hydrogen, ($C_1$-$C_6$)-alkanoyl, ($C_1$-$C_6$)-alkylcarbamoyl or another physiologically tolerated N$^{im}$ protective group which is acid-labile and/or can be eliminated under physiological conditions, $R^{10}$ and $R^{11}$ are identical or different and denote hydrogen, halogen, cyano, nitro, trifluoromethyl, ($C_1$-$C_6$)-alkyl, ($C_1$-$C_6$)-alkoxy, ($C_1$-$C_6$)-alkylmercapto, ($C_1$-$C_6$)-alkylcarbonyl, ($C_1$-$C_6$)-alkoxycarbonyl, ($C_1$-$C_6$)-alkylcarbonyloxy, ($C_3$-$C_8$)-cycloalkyl, phenyl, benzyl, benzyloxy, phenoxy, phenylmercapto, phenylsulfinyl, phenylsulfonyl, sulfamoyl, N-($C_1$-$C_4$)-alkylsulfamoyl or N,N-di-($C_1$-$C_4$)-alkylsulfamoyl, or, if A is defined as above under (a) or (c), can also together denote —[CH$_2$]$_n$— with n denoting 3, 4, 5 or 6, and one or two non-adjacent CH$_2$ groups optionally being replaced by oxygen, $R^{12}$ denotes hydrogen, ($C_1$-$C_4$)-alkyl or acyl, $R^{13}$ denotes ($C_1$-$C_5$)-alkyl, ($C_5$ or $C_6$)-cycloalkyl, hydroxyl, ($C_1$-$C_4$)-alkoxy or —NR$^{14}$R$^{15}$, $R^{14}$ and $R^{15}$ are identical or different and denote hydrogen, ($C_1$-$C_4$)-alkyl or phenyl which can be mono-, di- or trisubstituted by ($C_1$-$C_3$)-alkyl, ($C_1$-$C_4$)-alkoxy, trifluoromethyl and/or halogen, or $R^{14}$ and $R^{15}$ together represent a methylene chain —[CH$_2$]$_q$—, in which q is 3, 4, 5 or 6, and a methylene group can be replaced by oxygen, and to their physiologically tolerated salts.

1H-Thieno[3,4-d]imidazole-toluidine derivatives of the formula I in which A is defined as above under (b) are preferred.

T is preferably an —SO— group.

Also preferred are those compounds in which $R^1$ and $R^2$ are identical or different and denote hydrogen or ($C_1$-$C_4$)-alkyl, or together represent a methylene chain —[CH$_2$]$_n$— with n representing 4 or 5, in which a methylene group can be replaced by oxygen, $R^3$, $R^4$, $R^5$ and $R^6$ are identical or different and denote hydrogen, ($C_1$-$C_4$)-alkyl or ($C_1$-$C_4$)-alkoxy, $R^7$ and $R^8$ represent hydrogen, and $R^{10}$ and $R^{11}$ are identical or different and denote hydrogen, methyl or methoxy.

Compounds of the formula I which may be emphasized are those in which $R^9$ denotes hydrogen or a physiologically tolerated N$^{im}$ protective group which is acid-labile and/or can be eliminated under physiological conditions, in particular ($C_1$-$C_6$)-alkanoyloxy.

Particularly preferred 1H-thieno[3,4-d]imidazle-toluidine derivatives of the formula I are those in which A is preferably as defined under (b), T preferably denotes an —SO— group, $R^1$ and $R^2$ are identical or different and denote methyl or ethyl, $R^3$, $R^4$, $R^5$ and $R^6$ represent hydrogen, or 1 or 2 of these radicals represent(s) ($C_1$-$C_4$)-alkyl, in particular methyl, $R^7$ and $R^8$ each represent hydrogen, $R^9$ denotes hydrogen or ($C_1$-$C_6$)-alkanoyloxy, and $R^{10}$ and $R^{11}$ are identical or different and denote methyl or methoxy, in particular 2-(2-dimethylaminobenzylsulfinyl)-1H-thieno[3,4-d]imidazole and 2-(2-diethylaminobenzylsulfinyl)-1H-thieno[3,4-d]imidazole.

In this connection, halogen represents fluorine, chlorine, bromine or iodine.

A N$^{im}$ protective group which is acid-labile and/or which can be eliminated under physiological conditions is to be understood to include, for example, the alkanoyl and alkylcarbamoyl radicals already mentioned, as well as acetyl, trifluoroacetyl, trimethylsilylethoxycarbonyl, ($C_1$-$C_6$)-alkanoyloxy, vinyloxycarbonyl, and groups of the urethane type which can be eliminated with acid, such as Boc, Bpoc, Moc and Pyoc (cf. for example Kontakte Merck 3/79, pages 14 and 16–19; Kontakte Merck 1/80, page 31; Schröder, Lübke, The Peptides Vol. I New York, London 1965, pages 3–50).

Any chiral carbon and sulfur atoms which are present may occur both in the R and in the S configuration. In such cases, compounds of the formula I are in the form of a mixture of stereoisomers (such as a mixture of enantiomers and a mixture of diastereomers).

Particularly suitable salts are alkali metal and alkaline earth metal salts.

The invention also relates to a process for the preparation of compounds of the formula I, which comprises reacting compounds of the formula II

in which

A represents

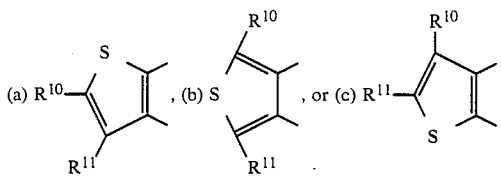

and $R^9$ denotes hydrogen, $(C_1-C_6)$-alkanoyl, $(C_1-C_6)$-alkylcarbamoyl or another physiologically tolerated $N^{im}$ protective group which is acid-labile and/or can be eliminated under physiological conditions, and $X^1$ denotes
i. a leaving group, or
ii. —SH or —S⁻, with a compound of the formula III

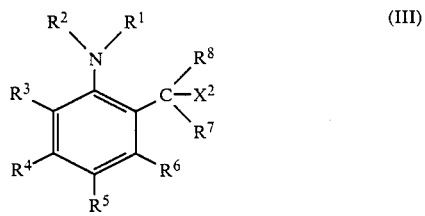

in which $R^1$ and $R^2$ are identical or different and denote hydrogen, $(C_1-C_6)$-alkyl, $(C_3-C_6)$-cycloalkyl, $(C_3-C_6)$-alkenyl or $(C_3-C_6)$-alkynyl, or $R^1$ and $R^2$ together represent a methylene chain —$[CH_2]_n$—, which can contain a double bond, in which n is 2, 3, 4, 5 or 6, and in which a methylene group can be replaced by oxygen, sulfur or $NR^{12}$, $R^3$, $R^4$, $R^5$ and $R^6$ are identical or different and represent hydrogen, halogen, cyano, trifluoromethyl, benzyloxy, $(C_1-C_6)$-alkyl-Y or phenyl-Y, in which Y denotes oxygen, sulfur, sulfinyl, sulfonyl or —$[CH_2]_m$— with m denoting 0, 1 or 2, —CO—$R^{13}$, —$SO_2NR^{14}R^{15}$, —O—$COR^{14}$, —$NR^{14}$—$COR^{15}$, —$NR^{14}$—$SO_2R^{15}$ or —$NR^{14}R^{15}$, $R^7$ and $R^8$ are identical or different and denote hydrogen or methyl, and $X^2$ denotes in the abovementioned case i. —SH or —S⁻, and in the abovementioned case ii. a leaving group, and i. if desired, oxidation of (a) —S— group which is present where appropriate in compounds of the formula I to give the —S— group, ii. if desired, reduction of (a) —SO— group which is present where appropriate in compunds of the formula I to give the —S— group, iii. if desired, acylation of compounds of the formula I in which $R^9$ represents hydrogen, iv. if desired, hydrolysis of compounds of the formula I in which $R^9$ does not denote hydrogen, and v. if desired, conversion of compounds of the formula I into their physiologically tolerated salts, it also being possible for two or more of the measures i.-iv. to be carried out in a sequence other than that given.

If, according to process variant (a) given here, compounds of the formula II are reacted with compounds of the formula III , then $X^1$ or $X^2$ represents a leaving group which can be detached nucleophilically, such as Cl, Br, I, —O—$SO_2CH_3$, —O—$SO_2$—$CF_3$ or —O—$SO_2$—$(C_6H_4$—$pCH_3)$.

The reaction of a compound of the formula II with a compound of the formula III, or its salts, is carried out in an inert solvent such as, for example, water, methylene chloride, methanol, ethanol, acetone, ethyl acetate, toluene, tetrahydrofuran, acetonitrile, dimethylformamide, dimethyl sulfoxide or mixtures of these solvents, expediently in the presence of an inorganic or organic base such as, for example, sodium or potassium hydroxide, carbonate, alkoxide, hydride or amide, ammonia, triethylamine, tributylamine or pyridine, at $-20°$ C. to $+150°$ C., preferably at $0°-80°$ C.

The compounds of the formula II can be prepared in analogy to known processes, for example by ring-closure of appropriately substituted o-diaminothiophenes with carbon disulfide (for example DE-A 3,132,167).

The 2,3-, 3,4- or 4,5-diaminothiophenes required for this purpose are either known from the literature or can be prepared in analogy to known processes. They are obtained by, for example, a reduction of appropriately substituted aminonitrothiophenes.

The compounds of the formula I obtained in this way can, if $R^9$ denotes hydrogen, be converted into physiologically tolerated salts.

Compounds of the formula I with T=—S— can furthermore be converted with suitable oxidizing agents into those with T=—SO— or —$SO_2$—.

This reaction is carried out in a suitable inert solvent such as, for example, methylene chloride, chloroform, carbon tetrachloride, 1,2-dichloroethane, toluene, ethyl acetate, acetic acid, trifluoroacetic acid, water, methanol, ethanol or mixtures thereof, at $-20°$ C. to $+150°$ C., preferably at $-10°$ C. to $+40°$ C.

Examples of suitable oxidizing agents are: hydrogen peroxide, peracids and peresters such as peracetic acid, trifluoroperacetic acid, monoperphthalic acid, m-chloroperbenzoic acid and their esters, ozone, dinitrogen tetroxide, iodosobenzene, N-chlorosuccinimide, 1-chlorobenzotriazole, sodium hypochlorite, potassium peroxodisulfate, t-butyl hypochlorite, tetrabutylammonium periodate or permanganate, 2-arylsulfonyl-3-aryloxaziridines, sodium metaperiodate, selenium dioxide or manganese dioxide, ceric ammonium nitrate, chromic acid, chlorine, bromine, diazabicyclo[2.2.2]octane/bromine complex, dioxane dibromide, pyridinium bromide perbromide, sulfuryl chloride, titanium tetra isopropylate/tert.-butyl hydroperoxide (where appropriate with the addition of dialkyl esters of (R)- and (L)-tartaric acid and, where appropriate, with the addition of a defined amount of water).

It is likewise possible to use isolated or, where appropriate, immobilized oxidizing enzymes or microorganisms as the oxidizing agent.

In the oxidation to T=—SO—, the oxidizing agents are used in equimolar amounts, where appropriate also in a slight excess of 5–10 mol-% or, if oxidation to T=—SO$_2$— is desired, they are also used in greater excess and/or at higher reaction temperature.

The following are compounds according to the invention which may be mentioned, without confining the invention to them.

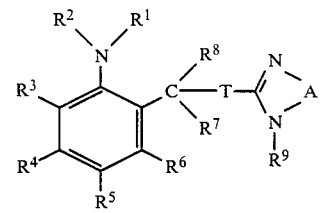

R$^7$, R$^8$, R$^9$ = H
T = S

| R$^1$ | R$^2$ | R$^3$ | R$^4$ | R$^5$ | R$^6$ | R$^{10}$ | R$^{11}$ |
|---|---|---|---|---|---|---|---|
| H | H | H | Me | H | H | H | H |
| Me | H | H | Me | H | H | H | H |
| Me | H | H | Me | H | H | OMe | H |
| Me | H | H | Me | H | H | OEt | H |
| Me | H | H | Me | H | H | OMe | OMe |
| Me | H | Me | H | H | H | H | H |
| Me | H | Me | H | H | H | OMe | H |
| Me | H | Me | H | H | H | OEt | H |
| Me | H | H | H | Me | H | H | H |
| Me | H | H | H | Me | H | OMe | H |
| Me | H | H | H | Me | H | OEt | H |
| Me | H | H | H | Me | H | OMe | OMe |
| H | H | H | H | H | Me | H | H |
| Me | H | H | H | H | Me | H | H |
| Me | H | H | H | H | Me | OMe | H |
| H | H | Et | H | H | H | H | H |
| Me | H | Et | H | H | H | H | H |
| Me | H | H | Et | H | H | H | H |
| Me | H | H | H | Et | H | H | H |
| H | H | Cl | H | H | H | H | H |
| Me | H | Cl | H | H | H | H | H |
| Me | H | Cl | H | H | H | OMe | H |
| Me | H | Cl | H | H | H | OEt | H |

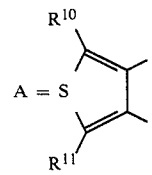

R$^7$, R$^8$, R$^9$ = H
T = S

| R$^1$ | R$^2$ | R$^3$ | R$^4$ | R$^5$ | R$^6$ | R$^{10}$ | R$^{11}$ |
|---|---|---|---|---|---|---|---|
| H | H | H | Cl | H | H | H | H |
| Me | H | H | Cl | H | H | H | H |
| Me | H | H | Cl | H | H | OEt | H |
| H | H | H | H | Cl | H | H | H |
| Me | H | H | H | Cl | H | H | H |
| Me | H | H | H | Cl | H | OMe | H |
| H | H | H | H | H | Cl | H | H |
| Me | H | H | H | H | Cl | H | H |
| H | H | Br | H | H | H | H | H |
| Me | H | Br | H | H | H | H | H |
| Me | H | Br | H | H | H | OEt | H |
| Me | H | H | Br | H | H | H | H |
| Me | H | H | H | Br | H | H | H |

-continued

| | | | | | | | |
|---|---|---|---|---|---|---|---|
| Me | H | H | H | Br | H | OEt | H |
| H | H | OMe | H | H | H | H | H |
| Me | H | OMe | H | H | H | H | H |
| Me | H | OMe | H | H | H | OEt | H |
| H | H | H | OMe | H | H | H | H |
| Me | H | H | OMe | H | H | H | H |
| H | H | H | H | OMe | H | H | H |
| Me | H | H | H | OMe | H | H | H |
| Me | H | H | H | OMe | H | OEt | H |
| Me | H | H | H | H | OMe | H | H |
| H | H | OEt | H | H | H | H | H |
| Me | H | OEt | H | H | H | H | H |
| Me | H | OEt | H | H | H | OEt | H |
| Me | H | H | OEt | H | H | H | H |
| Me | H | H | H | OEt | H | H | H |
| H | H | H | H | OEt | H | H | H |
| Me | H | H | H | OEt | H | OEt | H |
| Me | H | F | H | H | H | H | H |
| Me | H | H | F | H | H | H | H |
| Me | H | H | H | F | H | H | H |
| Me | H | H | H | H | F | H | H |
| H | H | Me | H | Me | H | H | H |
| Me | H | Me | H | Me | H | H | H |
| Me | H | Me | H | Me | H | OEt | H |
| Me | H | Me | Me | H | H | H | H |
| Me | H | Me | H | H | Me | H | H |
| Me | H | H | Me | Me | H | H | H |
| H | H | H | H | Me | Me | H | H |
| Me | H | H | H | Me | Me | H | H |
| H | H | Me | H | Cl | H | H | H |
| Me | H | Me | H | Cl | H | H | H |
| Me | H | Me | H | Cl | H | OEt | H |
| H | H | Cl | Cl | H | H | H | H |
| Me | H | Cl | Cl | H | H | H | H |
| H | H | Cl | H | Cl | H | H | H |
| Me | H | Cl | H | Cl | H | H | H |
| Me | H | Cl | H | Cl | H | OEt | H |
| Me | H | Cl | H | H | Cl | H | H |
| H | H | H | Cl | Cl | H | H | H |
| Me | H | H | Cl | Cl | H | H | H |
| Me | H | H | H | Cl | Cl | H | H |
| H | H | H | H | Cl | Cl | H | H |
| H | H | Br | H | Br | H | H | H |
| Me | H | Br | H | Br | H | H | H |
| H | H | Cl | H | OMe | H | H | H |
| Me | H | Cl | H | OMe | H | H | H |
| Me | H | Cl | H | OMe | H | OEt | H |
| H | H | OMe | H | Cl | H | H | H |
| Me | H | OMe | H | Cl | H | H | H |
| H | H | H | Cl | OMe | H | H | H |
| Me | H | H | Cl | OMe | H | H | H |
| H | H | H | H | OMe | Cl | H | H |
| Me | H | H | H | OMe | Cl | H | H |
| Me | H | H | H | OMe | Cl | OEt | H |
| H | H | Cl | H | OEt | H | H | H |
| Me | H | Cl | H | OEt | H | H | H |
| H | H | Br | H | OMe | H | H | H |
| Me | H | Br | H | OMe | H | H | H |
| H | H | Me | H | OMe | H | H | H |
| Me | H | Me | H | OMe | H | H | H |
| H | H | H | Me | OMe | H | H | H |
| Me | H | H | Me | OMe | H | H | H |
| H | H | H | H | OMe | Me | H | H |
| Me | H | H | H | OMe | Me | H | H |
| Me | H | H | H | OMe | Me | OEt | H |
| Me | H | H | H | OMe | Me | OMe | OMe |
| Me | H | H | H | OMe | Cl | OMe | OMe |
| Me | H | Cl | H | OEt | H | OMe | OMe |
| Me | H | Br | H | OMe | H | OMe | OMe |
| Me | H | Me | H | OMe | H | OMe | OMe |
| Me | H | Me | H | H | H | OMe | OMe |
| Me | H | H | Me | H | H | OMe | OMe |
| H | H | H | H | Me | H | OMe | OMe |
| Me | H | H | H | Me | H | OMe | OMe |
| Me | H | Et | H | H | H | OMe | OMe |
| Me | H | H | Et | H | H | OMe | OMe |
| Me | H | H | H | Et | H | OMe | OMe |
| Me | H | H | H | H | Me | OMe | OMe |
| H | H | Cl | H | H | H | OMe | OMe |
| Me | H | Cl | H | H | H | OMe | OMe |
| Me | H | H | Cl | H | H | OMe | OMe |
| H | H | H | H | Cl | H | OMe | OMe |

-continued

| | | | | | | | |
|---|---|---|---|---|---|---|---|
| Me | H | H | H | Cl | H | OMe | OMe |
| Me | H | H | H | H | Cl | OMe | OMe |
| Me | H | Br | H | H | H | OMe | OMe |
| Me | H | H | Br | H | H | OMe | OMe |
| Me | H | H | H | Br | H | OMe | OMe |
| Me | H | OMe | H | H | H | OMe | OMe |
| Et | H | H | H | OMe | Me | OMe | OMe |
| Et | H | H | H | OMe | Cl | OMe | OMe |
| Et | H | Cl | H | OEt | H | OMe | OMe |
| Et | H | Br | H | OMe | H | OMe | OMe |
| Et | H | Me | H | OMe | H | OMe | OMe |
| Et | H | Me | H | H | H | OMe | OMe |
| Et | H | H | Me | H | H | OMe | OMe |
| Et | H | H | H | Me | H | OMe | OMe |
| Et | H | Et | H | H | H | OMe | OMe |
| Et | H | H | Et | H | H | OMe | OMe |
| Et | H | H | H | Et | H | OMe | OMe |
| Et | H | H | H | H | Me | OMe | OMe |
| Et | H | Cl | H | H | H | OMe | OMe |
| Et | H | H | Cl | H | H | OMe | OMe |
| Et | H | H | H | Cl | H | OMe | OMe |
| Et | H | H | H | H | Cl | OMe | OMe |
| Et | H | Br | H | H | H | OMe | OMe |
| Et | H | H | Br | H | H | OMe | OMe |
| Et | H | H | H | Br | H | OMe | OMe |
| Et | H | OMe | H | H | H | OMe | OMe |
| Et | H | H | H | OMe | H | OMe | OMe |
| Et | H | H | H | OEt | H | OMe | OMe |
| Et | H | F | H | H | H | OMe | OMe |
| Et | H | H | F | H | H | OMe | OMe |
| Et | H | H | H | F | H | OMe | OMe |
| Et | H | H | H | H | F | OMe | OMe |
| Et | H | H | COOEt | H | H | OMe | OMe |
| Et | H | H | H | COOEt | H | OMe | OMe |
| Me | H | H | OMe | H | H | OMe | OMe |
| H | H | H | H | OMe | H | OMe | OMe |
| Me | H | H | H | OMe | H | OMe | OMe |
| Me | H | H | H | OEt | H | OMe | OMe |
| Me | H | F | H | H | H | OMe | OMe |
| ME | H | H | F | H | H | OMe | OMe |
| Me | H | H | H | F | H | OMe | OMe |
| Me | H | H | H | H | F | OMe | OMe |
| Me | H | Me | H | Me | H | OMe | OMe |
| Me | H | Me | Me | H | H | OMe | OMe |
| Me | H | H | Me | Me | H | OMe | OMe |
| Me | H | Me | H | Cl | H | OMe | OMe |
| Me | H | Cl | Cl | H | H | OMe | OMe |
| H | H | Cl | H | Cl | H | OMe | OMe |
| Me | H | Cl | H | Cl | H | OMe | OMe |
| Et | H | Cl | H | Cl | H | OMe | OMe |
| H | H | Cl | H | OMe | H | OMe | OMe |
| H | H | Cl | G | OMe | H | OMe | OMe |
| H | H | H | Cl | OMe | H | OMe | OMe |
| H | H | H | H | OMe | Cl | OMe | OMe |
| H | H | Cl | H | OEt | H | OMe | OMe |
| H | H | Br | H | OMe | H | OMe | OMe |
| Me | H | H | Me | Me | H | H | H |
| Me | H | H | Me | Me | Me | OMe | OMe |
| Me | H | H | OMe | Me | Me | H | H |
| Me | H | H | OMe | Me | Me | OMe | OMe |
| H | H | H | Me | OMe | Me | H | H |
| H | H | H | Me | OMe | Me | OMe | OMe |
| Me | H | H | Me | OMe | Me | H | H |
| Me | H | H | Me | OMe | Me | OMe | OMe |
| Me | H | H | Me | OMe | Me | OEt | H |
| Me | H | H | Cl | OMe | Cl | H | H |
| Me | H | H | Cl | OMe | Cl | OMe | OMe |
| Me | H | H | Me | Cl | Me | H | H |
| Me | H | H | Me | Cl | Me | OMe | OMe |
| Me | H | H | Cl | Me | Cl | H | H |
| H | —(CH$_2$)$_2$— | | H | H | H | H | H |
| H | —(CH$_2$)$_2$— | | H | H | H | OEt | H |
| H | —(CH$_2$)$_2$— | | H | H | H | OMe | OMe |
| H | —(CH$_2$)$_3$— | | H | H | H | H | H |
| H | —(CH$_2$)$_3$— | | H | H | H | OEt | H |
| H | —(CH$_2$)$_3$— | | H | H | H | OMe | OMe |
| H | —(CH$_2$)$_3$— | | H | OMe | H | H | H |
| H | —(CH$_2$)$_3$— | | H | OMe | H | OMe | OMe |
| —(CH$_2$)$_4$— | | H | H | H | H | H | H |
| —(CH$_2$)$_4$— | | Me | H | H | H | H | H |
| —(CH$_2$)$_4$— | | H | H | Me | H | H | H |
| —(CH$_2$)$_4$— | | H | H | OMe | H | H | H |

-continued

| R¹ | R² | R³ | R⁴ | R⁵ | R⁶ | R¹⁰ | R¹¹ |
|---|---|---|---|---|---|---|---|
| H | H | H | —(CH₂)₄— | | H | H | H |
| Me | H | H | —(CH₂)₄— | | H | H | H |
| Me | H | H | —(CH₂)₄— | | H | OMe | OMe |
| H | H | H | H | —(CH₂)₄— | | H | H |
| Me | H | H | H | —(CH₂)₄— | | H | H |
| Me | H | H | H | —(CH₂)₄— | | OMe | OMe |
| All | H | H | H | H | H | H | H |
| All | H | H | H | H | H | OMe | OMe |
| All | H | H | H | Me | H | H | H |
| All | H | H | H | Me | H | OMe | OMe |
| All | H | Me | H | H | H | H | H |
| All | H | Me | H | H | H | OEt | OEt |
| cPent | H | H | H | H | H | H | H |
| cPent | H | H | H | H | H | OEt | OEt |
| cPent | H | H | H | Me | H | H | H |
| Et | H | Me | H | Me | H | OMe | OMe |
| Et | H | Me | Me | H | H | OMe | OMe |
| Et | H | H | Me | Me | H | OMe | OMe |
| Et | H | Me | H | Cl | H | OMe | OMe |
| Et | H | Cl | Cl | H | H | OMe | OMe |

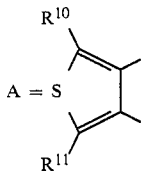

A = S

R⁷, R⁸, R⁹ = H
T = SO

| R¹ | R² | R³ | R⁴ | R⁵ | R⁶ | R¹⁰ | R¹¹ |
|---|---|---|---|---|---|---|---|
| Et | H | Me | H | Me | H | OMe | OMe |
| Et | H | Me | Me | H | H | OMe | OMe |
| Et | H | H | Me | Me | H | OMe | OMe |
| Et | H | Me | H | Cl | H | OMe | OMe |
| Et | H | Cl | Cl | H | H | OMe | OMe |
| H | H | H | Me | H | H | H | H |
| Me | H | H | Me | H | H | H | H |
| Me | H | H | Me | H | H | OMe | H |
| Me | H | H | Me | H | H | OEt | H |
| Me | H | H | Me | H | H | OMe | OMe |
| Me | H | Me | H | H | H | H | H |
| Me | H | Me | H | H | H | OMe | H |
| Me | H | Me | H | H | H | OEt | H |
| Me | H | H | H | Me | H | H | H |
| Me | H | H | H | Me | H | OMe | H |
| Me | H | H | H | Me | H | OEt | H |
| Me | H | H | H | Me | H | OMe | OMe |
| H | H | H | H | H | Me | H | H |
| Me | H | H | H | H | Me | H | H |
| Me | H | H | H | H | Me | OMe | H |
| H | H | Et | H | H | H | H | H |
| Me | H | Et | H | H | H | H | H |
| Me | H | H | Et | H | H | H | H |
| Me | H | H | H | Et | H | H | H |
| H | H | Cl | H | H | H | H | H |
| Me | H | Cl | H | H | H | H | H |
| Me | H | Cl | H | H | H | OMe | H |
| Me | H | Cl | H | H | H | OEt | H |
| H | H | H | Cl | H | H | H | H |
| Me | H | H | Cl | H | H | H | H |
| Me | H | H | Cl | H | H | OEt | H |
| H | H | H | H | Cl | H | H | H |
| Me | H | H | H | Cl | H | H | H |
| Me | H | H | H | Cl | H | OMe | H |
| H | H | H | H | H | Cl | H | H |
| Me | H | H | H | H | Cl | H | H |
| H | H | Br | H | H | H | H | H |
| Me | H | Br | H | H | H | H | H |
| Me | H | Br | H | H | H | OEt | H |
| Me | H | H | Br | H | H | H | H |
| Me | H | H | H | Br | H | H | H |
| Me | H | H | H | Br | H | OEt | H |
| H | H | OMe | H | H | H | H | H |
| Me | H | OMe | H | H | H | H | H |
| Me | H | OMe | H | H | H | OEt | H |
| H | H | H | OMe | H | H | H | H |
| Me | H | H | OMe | H | H | H | H |
| H | H | H | H | OMe | H | H | H |

-continued

| | | | | | | | |
|---|---|---|---|---|---|---|---|
| Me | H | H | H | OMe | H | H | H |
| Me | H | H | H | OMe | H | OEt | H |
| Me | H | H | H | H | OMe | H | H |
| H | H | OEt | H | H | H | H | H |
| Me | H | OEt | H | H | H | H | H |
| Me | H | OEt | H | H | H | OEt | H |
| Me | H | H | OEt | H | H | H | H |
| Me | H | H | H | OEt | H | H | H |
| H | H | H | H | OEt | H | H | H |
| Me | H | H | H | OEt | H | OEt | H |
| Me | H | F | H | H | H | H | H |
| Me | H | H | F | H | H | H | H |
| Me | H | H | H | F | H | H | H |
| Me | H | H | H | H | F | H | H |
| H | H | Me | H | Me | H | H | H |
| Me | H | Me | H | Me | H | H | H |
| Me | H | Me | H | Me | H | OEt | H |
| Me | H | Me | Me | H | H | H | H |
| Me | H | Me | H | H | Me | H | H |
| Me | H | H | Me | Me | H | H | H |
| H | H | H | H | Me | Me | H | H |
| Me | H | H | H | Me | Me | H | H |
| H | H | Me | H | Cl | H | H | H |
| Me | H | Me | H | Cl | H | H | H |
| Me | H | Me | H | Cl | H | OEt | H |
| H | H | Cl | Cl | H | H | H | H |
| Me | H | Cl | Cl | H | H | H | H |
| H | H | Cl | H | Cl | H | H | H |
| Me | H | Cl | H | Cl | H | H | H |
| Me | H | Cl | H | Cl | H | OEt | H |
| Me | H | Cl | H | H | Cl | H | H |
| H | H | H | Cl | Cl | H | H | H |
| Me | H | H | Cl | Cl | H | H | H |
| Me | H | H | H | Cl | Cl | H | H |
| H | H | H | H | Cl | Cl | H | H |
| H | H | Br | H | Br | H | H | H |
| Me | H | Br | H | Br | H | H | H |
| H | H | Cl | H | OMe | H | H | H |
| Me | H | Cl | H | OMe | H | H | H |
| Me | H | Cl | H | OMe | H | OEt | H |
| H | H | OMe | H | Cl | H | H | H |
| Me | H | OMe | H | Cl | H | H | H |
| H | H | H | Cl | OMe | H | H | H |
| Me | H | H | Cl | OMe | H | H | H |
| H | H | H | H | OMe | Cl | H | H |
| Me | H | H | H | OMe | Cl | H | H |
| Me | H | H | H | OMe | Cl | OEt | H |
| H | H | Cl | H | OEt | H | H | H |
| Me | H | Cl | H | OEt | H | H | H |
| H | H | Br | H | OMe | H | H | H |
| Me | H | Br | H | OMe | H | H | H |
| H | H | Me | H | OMe | H | H | H |
| Me | H | Me | H | OMe | H | H | H |
| H | H | H | Me | OMe | H | H | H |
| Me | H | H | Me | OMe | H | H | H |
| H | H | H | H | OMe | Me | H | H |
| Me | H | H | H | OMe | Me | H | H |
| Me | H | H | H | OMe | Me | OEt | H |
| Me | H | H | H | OMe | Me | OMe | OMe |
| Me | H | H | H | OMe | Cl | OMe | OMe |
| Me | H | Cl | H | OEt | H | OMe | OMe |
| Me | H | Br | H | OMe | H | OMe | OMe |
| Me | H | Me | H | OMe | H | OMe | OMe |
| Me | H | Me | H | H | H | OMe | OMe |
| Me | H | H | Me | H | H | OMe | OMe |
| H | H | H | H | Me | | OMe | OMe |
| Me | H | H | H | Me | H | OMe | OMe |
| Me | H | Et | H | H | H | OMe | OMe |
| Me | H | H | Et | H | H | OMe | OMe |
| Me | H | H | H | Et | H | OMe | OMe |
| Me | H | H | H | H | Me | OMe | OMe |
| H | H | Cl | H | H | H | OMe | OMe |
| Me | H | Cl | H | H | H | OMe | OMe |
| Me | H | H | Cl | H | H | OMe | OMe |
| H | H | H | H | Cl | H | OMe | OMe |
| Me | H | H | H | Cl | H | OMe | OMe |
| Me | H | H | H | H | Cl | OMe | OMe |
| Me | H | Br | H | H | H | OMe | OMe |
| Me | H | H | Br | H | H | OMe | OMe |
| Me | H | H | H | Br | H | OMe | OMe |
| Me | H | OMe | H | H | H | OMe | OMe |
| Et | H | H | H | OMe | Me | OMe | OMe |

-continued

| | | | | | | | |
|---|---|---|---|---|---|---|---|
| Et | H | H | H | OMe | Cl | OMe | OMe |
| Et | H | Cl | H | OEt | H | OMe | OMe |
| Et | H | Br | H | OMe | H | OMe | OMe |
| Et | H | Me | H | OMe | H | OMe | OMe |
| Et | H | Me | H | H | H | OMe | OMe |
| Et | H | H | Me | H | H | OMe | OMe |
| Et | H | H | H | Me | H | OMe | OMe |
| Et | H | Et | H | H | H | OMe | OMe |
| Et | H | H | Et | H | H | OMe | OMe |
| Et | H | H | H | Et | H | OMe | OMe |
| Et | H | H | H | H | Me | OMe | OMe |
| Et | H | Cl | H | H | H | OMe | OMe |
| Et | H | H | Cl | H | H | OMe | OMe |
| Et | H | H | H | Cl | H | OMe | OMe |
| Et | H | H | H | H | Cl | OMe | OMe |
| Et | H | Br | H | H | H | OMe | OMe |
| Et | H | H | Br | H | H | OMe | OMe |
| Et | H | H | H | Br | H | OMe | OMe |
| Et | H | OMe | H | H | H | OMe | OMe |
| Et | H | H | OMe | H | H | OMe | OMe |
| Et | H | H | H | OMe | H | OMe | OMe |
| Et | H | H | H | OEt | H | OMe | OMe |
| Et | H | F | H | H | H | OMe | OMe |
| Et | H | H | F | H | H | OMe | OMe |
| Et | H | H | H | F | H | OMe | OMe |
| Et | H | H | H | H | F | OMe | OMe |
| Me | H | H | OMe | H | H | OMe | OMe |
| H | H | H | H | OMe | H | OMe | OMe |
| Me | H | H | H | OMe | H | OMe | OMe |
| Me | H | H | H | OEt | H | OMe | OMe |
| Me | H | F | H | H | H | OMe | OMe |
| ME | H | H | F | H | H | OMe | OMe |
| Me | H | H | H | F | H | OMe | OMe |
| Me | H | H | H | H | F | OMe | OMe |
| Me | H | Me | H | Me | H | OMe | OMe |
| Me | H | Me | Me | H | H | OMe | OMe |
| Me | H | H | Me | Me | H | OMe | OMe |
| Me | H | Me | H | Cl | H | OMe | OMe |
| Me | H | Cl | Cl | H | H | OMe | OMe |
| H | H | Cl | H | Cl | H | OMe | OMe |
| Me | H | Cl | H | Cl | H | OMe | OMe |
| Et | H | Cl | H | Cl | H | OMe | OMe |
| H | H | Cl | H | OMe | H | OMe | OMe |
| H | H | Cl | G | OMe | H | OMe | OMe |
| H | H | H | Cl | OMe | H | OMe | OMe |
| H | H | H | H | OMe | Cl | OMe | OMe |
| H | H | Cl | H | OEt | H | OMe | OMe |
| H | H | Br | H | OMe | H | OMe | OMe |
| Me | H | H | Me | Me | H | H | H |
| Me | H | H | Me | Me | Me | OMe | OMe |
| Me | H | H | OMe | Me | Me | H | H |
| Me | H | H | OMe | Me | Me | OMe | OMe |
| H | H | H | Me | OMe | Me | H | H |
| H | H | H | Me | OMe | Me | OMe | OMe |
| Me | H | H | Me | Me | Me | H | H |
| Me | H | H | Me | OMe | Me | OMe | OMe |
| Me | H | H | Me | OMe | Me | OEt | H |
| Me | H | H | Cl | OMe | Cl | H | H |
| Me | H | H | Cl | OMe | Cl | OMe | OMe |
| Me | H | H | Me | Cl | Me | H | H |
| Me | H | H | Me | Cl | Me | OMe | OMe |
| Me | H | H | Cl | Me | Cl | H | H |
| H | —(CH$_2$)$_2$— | | H | H | H | H | H |
| H | —(CH$_2$)$_2$— | | H | H | H | OEt | H |
| H | —(CH$_2$)$_2$— | | H | H | H | OMe | OMe |
| H | —(CH$_2$)$_3$— | | H | H | H | H | H |
| H | —(CH$_2$)$_3$— | | H | H | H | OEt | H |
| H | —(CH$_2$)$_3$— | | H | H | H | OMe | OMe |
| H | —(CH$_2$)$_3$— | | H | OMe | H | H | H |
| H | —(CH$_2$)$_3$— | | H | OMe | H | OMe | OMe |
| —(CH$_2$)$_4$— | | H | H | H | H | H | H |
| —(CH$_2$)$_4$— | | Me | H | H | H | H | H |
| —(CH$_2$)$_4$— | | H | H | Me | H | H | H |
| —(CH$_2$)$_4$— | | H | H | OMe | H | H | H |
| H | H | H | —(CH$_2$)$_4$— | | H | H | H |
| Me | H | H | —(CH$_2$)$_4$— | | H | H | H |
| Me | H | H | —(CH$_2$)$_4$— | | H | OMe | OMe |
| H | H | H | H | H | —(CH$_2$)$_4$— | H | H |
| Me | H | H | H | H | —(CH$_2$)$_4$— | H | H |
| Me | H | H | H | H | —(CH$_2$)$_4$— | OMe | OMe |
| All | H | H | H | H | H | H | H |
| All | H | H | H | H | H | OMe | OMe |

| | | | | | | | |
|---|---|---|---|---|---|---|---|
| All | H | H | H | Me | H | H | H |
| All | H | H | H | Me | H | OMe | OMe |
| All | H | Me | H | H | H | H | H |
| All | H | Me | H | H | H | OEt | OEt |
| cPent | H | H | H | H | H | H | H |
| cPent | H | H | H | H | H | OEt | OEt |
| cPent | H | H | H | Me | H | H | H |

Abbreviations:
Me methyl
Et ethyl
All allyl
cPent cyclopentyl

The new compounds of the formula I and their salts have valuable pharmacological properties.

They markedly inhibit gastric acid secretion and, furthermore, exhibit an excellent protective action on the stomach and intestines.

"Protection of the stomach and intestines" in this connection is to be understood to be the prevention and treatment of gastrointestinal disorders, especially gastrointestinal inflammatory disorders and lesions (such as, for example, gastric ulcer, duodenal ulcer, gastritis, and hyperacidic or drug-related functional gastropathy) which may be caused by, for example, microorganisms, bacterial toxins, drugs (for example antiinflammatory and antirheumatic agents), chemicals (for example ethanol), gastric acid or stress situations.

By reason of their excellent properties, the substituted thienoimidazoles of the formula I and their pharmacologically tolerated salts are outstandingly suitable for use in human and veterinary medicine, being particularly used for the treatment and prophylaxis of disorders of the stomach and intestines and those disorders deriving from excessive gastric acid secretion.

Hence the invention also relates to the compounds of the formula I, according to the invention, for use for the treatment and prophylaxis of the abovementioned disorders.

The invention likewise embraces the use of the compounds according to the invention for the preparation of medicaments used for the treatment and prophylaxis of the abovementioned disorders.

The invention further relates to medicaments containing one or more compounds of the general formula I and/or their pharmacologically tolerated salts.

The medicaments are prepared by processes which are known per se and familiar to the expert. The pharmacologically effective compounds (=active substances) are used as medicaments according to the invention either as such or, preferably, in combination with suitable pharmaceutical auxiliaries, in the form of tablets, coated tablets, capsules suppositories, emulsions, suspensions or solutions, the content of active substance advantageously being between 0.1 and 96% by weight.

The auxiliaries suitable for the desired medicament formulations are familiar to the expert on the basis of his knowledge. Besides solvents, gel-forming agents, suppository bases, tabletting auxiliaries and other active substance excipients, it is possible to use, for example, antioxidants, dispersions, emulsifiers, antifoam agents, flavorings, preservatives, solubilizers or colorants.

The active substances can be administered orally or parenterally, preference being given to oral administration.

In general, it has proved advantageous in human medicine to administer the active substance or substances, when given orally, in a daily dose of about 0.01 to about 20 mk/kg of body weight, where appropriate in the form of several, preferably 1 to 4, individual doses to achieve the desired results. On parenteral administration it is possible to use similar or (especially on intravenous administration of the active substances) as a rule lower dosages. Any expert is readily able, on the basis of his specialist knowledge, to establish the optimal dosage and mode of administration of the active substances which are necessary in each case.

If the compounds according to the invention and/or their salts are to be used to treat the abovementioned disorders, it is also possible for the pharmacetuical compositions to contain one or more pharmacologically active ingredients from other medicament groups, such as antacids, for example aluminum hydroxide or magnesium aluminate; tranquilizers such as benzoidiazepines, for example diazepam; spasmolytics such as, for example, bietamiverine or camylofin; anticholinergics such as, for example, oxyphencyclimine or phencarbamide; local anesthetics such as, for example, tetracaine or procaine; and, where appropriate, enzymes, vitamins or amino acids.

For a form for oral use, the active compounds are mixed with the additives customary for this purpose, such as vehicles, stabilizers or inert diluents, and converted by customary methods into suitable forms for administration, such as tablets, coated tablets, hard gelatin capsules, aqueous, alcoholic or oily suspensions or aqueous, alcoholic or oily solutions. Examples of inert excipients which can be used are gum arabic, magnesia, magnesium carbonate, lactose, sucrose or starch, especially corn starch. This preparation can be carried out either as dry or wet granules. Examples of suitable oily vehicles or solvents are vegetable or animal oils, such as sunflower oil or fish liver oil.

For subcutaneous or intravenous administration the active compounds or their physiologically tolerated salts are converted into a solution, suspension or emulsion, if desired with the substances customary for this purpose, such as solubilizers, emulsifiers or other auxiliaries. Examples of suitable solvents for the new active compounds and the corresponding physiologically tolerated salts are: water, physiological saline solutions or alcohols, for example ethanol, propanol or glycerol, as well as sugar solutions such as glucose or mannitol solutions, or a mixture of the various solvents mentioned.

The examples which are detailed hereinafter serve to illustrate the invention but without restricting it. The stated melting and decomposition points have not been corrected or standardized.

EXAMPLE 1

2-(2-Dimethylaminobenzylmercapto)-1H-thieno[3,4-d]imidazole 2.9 g of 2-dimethylaminobenzyl bromide hydrobromide are added to a solution of 1.56 g of 2-mercaptothieno[3,4-d]imidazole in 20 ml of anhydrous dimethylacetamide. A crystalline precipitate separates out in a weakly exothermic reaction. The mixture is stirred at room temperature for one hour, acetone is added, and the crystals are filtered off and dried in a stream of air. The crystalline solid is then introduced into saturated aqueous NaHCO$_3$ solution, the mixture is heated briefly on a steam bath and, after stirring at room temperature, the crystals are filtered off. Treatment with active charcoal in ethanol and concentration is followed by solution being induced to crystallize with a little acetone.

Crystalline substance, melting point 124°–131° C.

EXAMPLE 2

2-(2-Dimethylaminobenzylsulfinyl)-1H-thieno[3,4-d]imidazole

A solution of 0.28 g of 2-(2-dimethylaminobenzylmercapto)-1H-thieno[3,4-d]imidazole in 50 ml of methylene chloride is treated successively with 50 ml of saturated sodium bicarbonate solution and, after cooling to 0° to 5° C. with stirring, a solution of 0.2 g of 3-chloroperbenzoic acid (85% pure) in methylene chloride. The oganic phase is separated off and distilled, and then the residue is chromatographed on silica gel (mobile phase ethyl acetate/methanol=1:1).

Crystals, melting point 120° C. (decomposition).

EXAMPLE 3

2-(2-Diethylaminobenzylmercapto)-1H-thieno[3,4-d]imidazole 1.47 g of 2-mercaptothieno[3,4-d]imidazole are reacted with 3.05 g of 2-diethylaminobenzyl bromide hydrobromide, and the product is worked up in analogy to the procedure described in Example 1.

Crystalline solid, melting point 124° C. (decomposition).

EXAMPLE 4

2-(2-Diethylaminobenzylsulfinyl)-1H-thieno[3,4-d]imidazole 1.6 g of 2-(2-diethylaminobenzylmercapto)-1H-thieno[3,4-d]imidazole are reacted, and the product is worked up, in analogy to the procedure given in Example 2.

Crystalline solid, melting point 155° C. (decomposition).

EXAMPLE 5

2-(2-Ethylaminobenzylmercapto)-1H-thieno[3,4-d]imidazole 1.12 g of 2-ethylaminobenzyl bromide hydrobromide are added to a solution of 0.60 g of 2-mercaptothieno[3,4-d]imidazole in 100 ml of acetone. After the mixture has been stirred at room temperature for 24 hours, the solvent is removed by distillation in vacuo, and the crystalline residue is washed with acetone. Then 1N NH$_4$OH solution is added to the product, the mixture is stirred for 2 hours, and the solid is filtered off with suction and washed wit water. The residue which has been dried in air is dissolved in methylene chloride, active charcoal is added, and the mixture is filtered. Concentration in vacuo results in the clorless crystalline product.

Melting point 230° C. (decomposition).

EXAMPLE 6

2-(2-Aminobenzylsulfinyl)-1H-thieno[3,4-d]imidazole sodium salt 1.3 ml of thionyl chloride are added dropwise, at −15° C. with stirring, to 1.50 g of 2-aminobenzyl alcohol in 30 ml of tetrahydrofuran, and stirring is then continued for 20 minutes. This solution is then slowly added, while cooling in ice, to a solution of 1.90 g of 2-mercaptothieno[3,4-d]imidazole in 30 ml of 2N NaOH and 50 ml of ethanol. The solution is concentrated at room temperature, water is added, the mixture is extracted four times with methylene chloride, the organic phase is dried over MgSO$_4$, and then the solvent is removed by distillation in vacuo.

The resulting mercapto compound (1.5 g) is dissolved in 30 ml of methylene chloride, and 30 ml of saturated aqueous NaHCO$_3$ solution are added. At 0° to −5° C., 0.60 g of m-chloroperbenzoic acid—dissolved in methylene chloride—is added dropwise, and the mixtures is then stirred for 20 minutes. A brown resin is subsequently removed, and a further 0.60 g of m-chloroperbenzoic acid is added.

The precipitated product is filtered off with suction and dried in a stream of air.

Melting point >270° C.

We claim:

1. A compound of the formula I

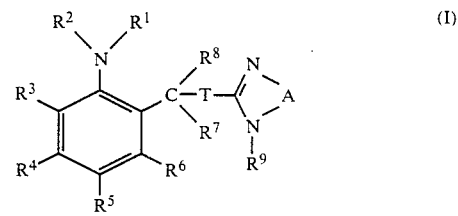

in which

A represents

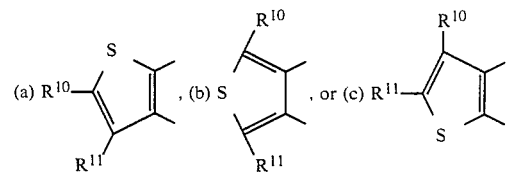

T is —S—, —SO— or —SO$_2$—,

R$^1$ and R$^2$ are identical or different and are hydrogen, (C$_1$–C$_6$)-alkyl, (C$_3$–C$_6$)-cycloalkyl, (C$_3$–C$_6$)-alkenyl or (C$_3$–C$_6$)-alkynyl, or R$^1$ and R$^2$ together represent a methylene chain —[CH$_2$]$_n$—, which can contain a double bond, in which n is 4 or 5, or represent said methylene chain in which, when n is 5, the CH$_2$ in para position to the N-atom to which R$^1$ and R$^2$ are attached is replaced by oxygen, sulfur or NR$^{12}$, R$^3$, R$^4$, R$^5$ and R$^6$ are identical or different and represent hydrogen, halogen, cyano, trifluoromethyl, benzyloxy, (C$_1$–C$_6$)-alkyl-Y or phenyl-Y, in which Y is oxygen, sulfur, sulfinyl, sulfonyl, or —[CH$_2$-

]$_m$— with m being 0, 1 or 2, —CO—R$^{13}$, —SO$_2$NR$^{14}$R$^{15}$, —O—COR$^{14}$, —NR$^{14}$—COR$^{15}$, —NR$^{14}$—SO$_2$R$^{15}$ or —NR$^{14}$R$^{15}$, R$^7$ and R$^8$ are identical or different and are hydrogen or methyl, R$^9$ is hydrogen, (C$_1$-C$_6$)-alkanoyl, (C$_1$-C$_6$)-alkyl-carbamoyl, or another physiologically tolerated N$^{im}$ protective group which is acid-labile and/or can be eliminated under physiological conditions, R$^{10}$ and R$^{11}$ are identical or different and are hydrogen, halogen, cyano, nitro, trifluoromethyl, (C$_1$-C$_6$)-alkyl, (C$_1$-C$_6$)-alkoxy, (C$_1$-C$_6$)-alkylmercapto, (C$_1$-C$_6$)-alkylcarbonyl, (C$_1$-C$_6$)-alkoxycarbonyl, (C$_1$-C$_6$)-alkylcarbonyloxy, (C$_3$-C$_8$)-cycloalkyl, phenyl, benzyl, benzyloxy, phenoxy, phenylmercapto, phenylsulfinyl, phenylsulfonyl, sulfamoyl, N-(C$_1$-C$_4$)-alkylsulfamoyl or N,N-di-(C$_1$-C$_4$)-alkylsulfamoyl, or, if A is defined as above under (a) or (c), can also together be a methylene chain —[CH$_2$]$_n$— wherein n is 3, 4, 5 or 6, or said methylene chain wherein one or two non-adjacent CH$_2$ groups is replaced by oxygen, R$^{12}$ is hydrogen, (C$_1$-C$_4$)-alkyl or (C$_1$-C$_4$)-acyl, R$^{13}$ is (C$_1$-C$_5$)-alkyl, (C$_5$ or C$_6$)-cycloalkyl, hydroxyl, (C$_1$-C$_4$)-alkoxy or —NR$^{14}$R$^{15}$, R$^{14}$ and R$^{15}$ are identical or different and are hydrogen, (C$_1$-C$_4$)-alkyl, phenyl or phenyl which is mono-, di-, or trisubstituted by (C$_1$-C$_3$)-alkyl, (C$_1$-C$_4$)-alkoxy, trifluoromethyl and/or halogen, or R$^{14}$ and R$^{15}$ together represent a methylene chain —[CH$_2$]$_q$—, in which q is 3, 4, 5 or 6, or said methylene chain wherein a methylene group is replaced by oxygen, or a physiologically tolerated salt thereof.

2. A compound of the formula I as claimed in claim 1, in which A is as defined in claim 1 under (b), or a physiologically tolerated salt thereof.

3. A compound of the formula I as claimed in claim 1, in which T represents —SO— or a physiologically tolerated salt thereof.

4. A compound of the formula I as claimed in claim 1, in which

R$^1$ and R$^2$ are identical or different and are hydrogen or (C$_1$-C$_4$)-alkyl, or together represent a methylene chain —[CH$_2$]$_n$— with n being 4 or 5, or said methylene chain in which, when n is 5, the CH$_2$ in para position to the N-atom to which R$^1$ and R$^2$ are attached, is replaced by oxygen, R$^3$, R$^4$, R$^5$ and R$^6$ are identical or different and are hydrogen, (C$_1$-C$_4$)-alkyl or (C$_1$-C$_4$)-alkoxy, R$^7$ and R$^8$ represent hydrogen, and R$^{10}$ and R$^{11}$ are identical or different and are hydrogen, methyl or methoxy, or a physiologically tolerated salt thereof.

5. A compound of the formula I as claimed in claim 1 in which

R$^9$ is hydrogen or a physiologically tolerated N$^{im}$ protective group which is acid-labile and/or can be eliminated under physiological conditions, or a physiologically tolerated salt thereof.

6. A compound of the formula I as claimed in claim 1 in which R$^9$ represents (C$_1$-C$_6$)-alkanoyloxy, or a physiologically tolerated salt thereof.

7. A compound of the formula I as claimed in claim 1 in which

A is as defined under (b),

T is an —SO— group,

R$^1$ and R$^2$ are identical or different and are methyl or ethyl,

R$^3$, R$^4$, R$^5$ and R$^6$ represent hydrogen, or 1 or 2 of these radicals represent(s) (C$_1$-C$_4$)-alkyl, R$^7$ and R$^8$ each is hydrogen, R$^9$ is hydrogen or (C$_1$-C$_6$)-alkanoyloxy, and R$^{10}$ and R$^{11}$ are identical or different and are methyl or methoxy, or a physiologically tolerated salt thereof.

8. 2-(2-Dimethylaminobenzylsulfinyl)-1H-thieno[3,4-d]imidazole or a physiologically tolerated salt thereof.

9. 2-(2-Diethylaminobenzylsulfinyl)-1H-thieno[3,4-d]imidazole or a physiologically tolerated salt thereof.

10. A compound of the formula I as claimed in claim 1, in which R$^1$ and R$^2$ together represent pyrrolidino, piperidino, morpholino, thiomorpholino or piperazino.

11. A pharmaceutical composition for the inhibition of gastric acid secretion comprising an effective amount of a compound of the formula I as claimed in claim 1, or its physiologically tolerated salt, and a physiologically acceptable excipient.

12. A process for inhibiting gastric acid secretion, which comprises administration to a host of an effective amount of a compound of the formula I as claimed in claim 1, or its physiologically tolerated salt.

* * * * *